(12) United States Patent
Pays

(10) Patent No.: US 9,119,817 B2
(45) Date of Patent: Sep. 1, 2015

(54) WILD-TYPE APOLIPOPROTEIN L-I FOR USE IN THE PREVENTION OF KIDNEY DISEASES

(75) Inventor: Etienne Pays, Nil-Saint-Vincent (BE)

(73) Assignee: UNIVERSITE LIBRE DE BRUXELLES, Brussels (BE)

(*) Notice: Subject to any disclaimer, the term of this patent is extended or adjusted under 35 U.S.C. 154(b) by 0 days.

(21) Appl. No.: 14/000,079

(22) PCT Filed: Feb. 17, 2012

(86) PCT No.: PCT/EP2012/052731
§ 371 (c)(1),
(2), (4) Date: Nov. 13, 2013

(87) PCT Pub. No.: WO2012/110625
PCT Pub. Date: Aug. 23, 2012

(65) Prior Publication Data
US 2014/0057849 A1    Feb. 27, 2014

(30) Foreign Application Priority Data
Feb. 17, 2011   (EP) ...................................... 11154776

(51) Int. Cl.
*A61K 38/17*   (2006.01)
*A61P 13/12*   (2006.01)

(52) U.S. Cl.
CPC .............. *A61K 38/1709* (2013.01); *A61K 38/17* (2013.01)

(58) Field of Classification Search
CPC ........................... A61K 38/17; A61K 38/1709
See application file for complete search history.

(56) References Cited

FOREIGN PATENT DOCUMENTS

| WO | WO 2004/012757 | 2/2004 |
|----|----------------|--------|
| WO | WO 2011/020497 | 2/2011 |
| WO | WO 2011/020865 | 2/2011 |

OTHER PUBLICATIONS

Uniprot Protein Database, protein accession No. 014791, Human Apolipoprotein L1, pp. 1-9, accessed on Jul. 21, 2014.*
OMIM Entry, 603743, Apolipoprotein L-I, pp. 1-4, accessed on Jul. 21, 2014.*
Glomerulonephritis Treatment and Drugs, Mayo Clinic Website, accessed Jul. 21, 2014.*
Genovese et al., "Association of Trypanolytic ApoL1 Variants with Kidney Disease in African Americans", *Science*, vol. 239, 2010, pp. 841-845.
Genovese et al., "A risk allele for focal segmental glomerulosclerosis in African Americans is located within a region containing APOL1 and MYH9", *Kidney International*, vol. 78, 2010, pp. 698-704.
International Search Report and Written Opinion from International Application No. PCT/EP2012/052731 mailed May 7, 2012.
Kronenberg, "APOL1 variants and kidney disease. There is no such thing as free lunch*", *Nephrology Dial Transplant*, vol. 26, 2011, pp. 775-778.
Lecordier et al., "C-Terminal Mutants of Apolipoprotein L-I Efficiently Kill Both *Trypanosoma brucei brucei* and *Trypanosoma brucei rhodesiense*", *PLOS Pathogens*, vol. 5, Issue 12, 2009, pp. 1-11.
Leslie, "Genetics. Kidney Disease Is Parasite-Slaying Protein's Downside", *Science*, vol. 329, 2010, pp. 263.
Tzur et al., "Missense mutations in the APOL1 gene are highly associated with end stage kidney disease risk previously attributed to the MYH9 gene", *Hum Genet*, vol. 128, 2010, pp. 345-350.
Wan et al., "Apolipoprotein L1, a Novel Bcl-2 Homology Domain 3-only Lipid-binding Protein, Induces Autophagic Cell Death", *The Journal of Biological Chemistry*, vol. 283, No. 31, 2008, pp. 21540-21549.

* cited by examiner

*Primary Examiner* — James H Alstrom Acevedo
*Assistant Examiner* — Erinne Dabkowski
(74) *Attorney, Agent, or Firm* — Merchant & Gould P.C.

(57) ABSTRACT

A wild-type human Apolipoprotein L-I is used in a method for the prevention and/or the treatment of renal disease.

13 Claims, No Drawings

SEQUENCE LISTING

```
<160> NUMBER OF SEQ ID NOS: 9

<210> SEQ ID NO 1
<211> LENGTH: 398
<212> TYPE: PRT
<213> ORGANISM: Homo sapiens

<400> SEQUENCE: 1

Met Glu Gly Ala Ala Leu Leu Arg Val Ser Val Leu Cys Ile Trp Met
1               5                   10                  15

Ser Ala Leu Phe Leu Gly Val Arg Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270
```

```
Tyr Gln Leu Thr Arg Gly Ile Gly Lys Asp Ile Arg Ala Leu Arg Arg
            275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
            355                 360                 365

Glu Glu Leu Lys Lys Val Ala Gln Glu Leu Glu Lys Leu Asn Ile
            370                 375                 380

Leu Asn Asn Asn Tyr Lys Ile Leu Gln Ala Asp Gln Glu Leu
385                 390                 395
```

<210> SEQ ID NO 2
<211> LENGTH: 396
<212> TYPE: PRT
<213> ORGANISM: Homo sapiens
<220> FEATURE:
<221> NAME/KEY: MISC_FEATURE
<222> LOCATION: (1)..(396)
<223> OTHER INFORMATION: Apo L 1 variant

<400> SEQUENCE: 2

```
Met Glu Gly Ala Ala Leu Leu Arg Val Ser Val Leu Cys Ile Trp Met
1               5                   10                  15

Ser Ala Leu Phe Leu Gly Val Arg Val Arg Ala Glu Glu Ala Gly Ala
            20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220
```

```
Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
370                 375                 380

Leu Asn Asn Lys Ile Leu Gln Ala Asp Gln Glu Leu
385                 390                 395

<210> SEQ ID NO 3
<211> LENGTH: 398
<212> TYPE: PRT
<213> ORGANISM: Homo sapiens
<220> FEATURE:
<221> NAME/KEY: MISC_FEATURE
<222> LOCATION: (1)..(398)
<223> OTHER INFORMATION: Apo L 1 Variant

<400> SEQUENCE: 3

Met Glu Gly Ala Ala Leu Leu Arg Val Ser Val Leu Cys Ile Trp Met
1               5                   10                  15

Ser Ala Leu Phe Leu Gly Val Arg Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Gly Lys Val Ser
65                  70                  75                  80

Thr Gln Asn Leu Leu Leu Leu Thr Asp Asn Glu Ala Trp Asn Gly
            85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
```

-continued

```
                180                 185                 190
Gly Met Gly Leu Ala Pro Phe Thr Glu Gly Gly Ser Leu Val Leu
            195                 200                 205
Glu Pro Gly Met Glu Leu Gly Ile Thr Ala Ala Leu Thr Gly Ile Thr
            210                 215                 220
Ser Ser Thr Ile Asp Tyr Gly Lys Lys Trp Trp Thr Gln Ala Gln Ala
225                 230                 235                 240
His Asp Leu Val Ile Lys Ser Leu Asp Lys Leu Lys Glu Val Lys Glu
                245                 250                 255
Phe Leu Gly Glu Asn Ile Ser Asn Phe Leu Ser Leu Ala Gly Asn Thr
                260                 265                 270
Tyr Gln Leu Thr Arg Gly Ile Gly Lys Asp Ile Arg Ala Leu Arg Arg
                275                 280                 285
Ala Arg Ala Asn Leu Gln Ser Val Pro His Ala Ser Ala Ser Arg Pro
                290                 295                 300
Arg Val Thr Glu Pro Ile Ser Ala Glu Ser Gly Glu Gln Val Glu Arg
305                 310                 315                 320
Val Asn Glu Pro Ser Ile Leu Glu Met Ser Arg Gly Val Lys Leu Thr
                325                 330                 335
Asp Val Ala Pro Val Gly Phe Phe Leu Val Leu Asp Val Val Tyr Leu
                340                 345                 350
Val Tyr Glu Ser Lys His Leu His Glu Gly Ala Lys Ser Glu Thr Ala
                355                 360                 365
Glu Glu Leu Lys Lys Val Ala Gln Leu Glu Glu Lys Leu Asn Met
                370                 375                 380
Leu Asn Asn Asn Tyr Lys Ile Leu Gln Ala Asp Gln Glu Leu
385                 390                 395
```

<210> SEQ ID NO 4
<211> LENGTH: 398
<212> TYPE: PRT
<213> ORGANISM: Homo sapiens
<220> FEATURE:
<221> NAME/KEY: MISC_FEATURE
<223> OTHER INFORMATION: NP 003652.2

<400> SEQUENCE: 4

```
Met Glu Gly Ala Ala Leu Leu Arg Val Ser Val Leu Cys Ile Trp Met
1               5                   10                  15
Ser Ala Leu Phe Leu Gly Val Gly Val Arg Ala Glu Glu Ala Gly Ala
                20                  25                  30
Arg Val Gln Gln Asn Val Pro Ser Gly Thr Asp Thr Gly Asp Pro Gln
                35                  40                  45
Ser Lys Pro Leu Gly Asp Trp Ala Ala Gly Thr Met Asp Pro Glu Ser
            50                  55                  60
Ser Ile Phe Ile Glu Asp Ala Ile Lys Tyr Phe Lys Glu Lys Val Ser
65                  70                  75                  80
Thr Gln Asn Leu Leu Leu Leu Thr Asp Asn Glu Ala Trp Asn Gly
                85                  90                  95
Phe Val Ala Ala Ala Glu Leu Pro Arg Asn Glu Ala Asp Glu Leu Arg
                100                 105                 110
Lys Ala Leu Asp Asn Leu Ala Arg Gln Met Ile Met Lys Asp Lys Asn
                115                 120                 125
Trp His Asp Lys Gly Gln Gln Tyr Arg Asn Trp Phe Leu Lys Glu Phe
            130                 135                 140
```

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
            165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Glu Lys Leu Asn Ile
    370                 375                 380

Leu Asn Asn Asn Tyr Lys Ile Leu Gln Ala Asp Gln Glu Leu
385                 390                 395

<210> SEQ ID NO 5
<211> LENGTH: 396
<212> TYPE: PRT
<213> ORGANISM: Homo sapiens
<220> FEATURE:
<221> NAME/KEY: MISC_FEATURE
<222> LOCATION: (1)..(396)
<223> OTHER INFORMATION: Apo L 1 Variant

<400> SEQUENCE: 5

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg

```
              100                 105                 110
Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
            130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
            165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
            195                 200                 205

Glu Pro Gly Met Glu Leu Gly Ile Thr Ala Ala Leu Thr Gly Ile Thr
            210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
            245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
            275                 280                 285

Ala Arg Ala Asn Leu Gln Ser Val Pro His Ala Ser Ala Ser Arg Pro
            290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
            325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
            355                 360                 365

Glu Glu Leu Lys Lys Val Ala Gln Glu Leu Glu Lys Leu Asn Ile
            370                 375                 380

Leu Asn Asn Lys Ile Leu Gln Ala Asp Gln Glu Leu
385                 390                 395

<210> SEQ ID NO 6
<211> LENGTH: 398
<212> TYPE: PRT
<213> ORGANISM: Homo sapiens
<220> FEATURE:
<221> NAME/KEY: MISC_FEATURE
<222> LOCATION: (1)..(398)
<223> OTHER INFORMATION: Apo L 1 Variant

<400> SEQUENCE: 6

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
            50                  55                  60
```

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
            85                  90                  95

Phe Val Ala Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
            130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
            195                 200                 205

Glu Pro Gly Met Glu Leu Gly Ile Thr Ala Ala Leu Thr Gly Ile Thr
210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
            275                 280                 285

Ala Arg Ala Asn Leu Gln Ser Val Pro His Ala Ser Ala Ser Arg Pro
290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Gly Phe Phe Leu Val Leu Asp Val Val Tyr Leu
            340                 345                 350

Val Tyr Glu Ser Lys His Leu His Glu Gly Ala Lys Ser Glu Thr Ala
            355                 360                 365

Glu Glu Leu Lys Lys Val Ala Gln Glu Leu Glu Lys Leu Asn Met
370                 375                 380

Leu Asn Asn Asn Tyr Lys Ile Leu Gln Ala Asp Gln Glu Leu
385                 390                 395

<210> SEQ ID NO 7
<211> LENGTH: 398
<212> TYPE: PRT
<213> ORGANISM: Homo sapiens

<400> SEQUENCE: 7

Met Glu Gly Ala Ala Leu Leu Arg Val Ser Val Leu Cys Ile Trp Met
1               5                   10                  15

Ser Ala Leu Phe Leu Gly Val Arg Val Arg Ala Glu Glu Ala Gly Ala
            20                  25                  30

Arg Val Gln Gln Asn Val Pro Ser Gly Thr Asp Thr Gly Asp Pro Gln

```
            35                  40                  45
Ser Lys Pro Leu Gly Asp Trp Ala Ala Gly Thr Met Asp Pro Glu Ser
 50                  55                  60
Ser Ile Phe Ile Glu Asp Ala Ile Lys Tyr Phe Lys Glu Lys Val Ser
 65                  70                  75                  80
Ile Gln Asn Leu Leu Leu Leu Thr Asp Asn Glu Ala Trp Asn Gly
                 85                  90                  95
Phe Val Ala Ala Ala Glu Leu Pro Arg Asn Glu Ala Asp Glu Leu Arg
                100                 105                 110
Lys Ala Leu Asp Asn Leu Ala Arg Gln Met Ile Met Lys Asp Lys Asn
                115                 120                 125
Trp His Asp Lys Gly Gln Gln Tyr Arg Asn Trp Phe Leu Lys Glu Phe
 130                 135                 140
Pro Arg Leu Lys Ser Lys Leu Glu Asp Asn Ile Arg Arg Leu Arg Ala
 145                 150                 155                 160
Leu Ala Asp Gly Val Gln Lys Val His Lys Gly Thr Thr Ile Ala Asn
                165                 170                 175
Val Val Ser Gly Ser Leu Ser Ile Ser Ser Gly Ile Leu Thr Leu Val
                180                 185                 190
Gly Met Gly Leu Ala Pro Phe Thr Glu Gly Gly Ser Leu Val Leu Leu
            195                 200                 205
Glu Pro Gly Met Glu Leu Gly Ile Thr Ala Ala Leu Thr Gly Ile Thr
 210                 215                 220
Ser Ser Thr Ile Asp Tyr Gly Lys Lys Trp Trp Thr Gln Ala Gln Ala
 225                 230                 235                 240
His Asp Leu Val Ile Lys Ser Leu Asp Lys Leu Lys Glu Val Lys Glu
                245                 250                 255
Phe Leu Gly Glu Asn Ile Ser Asn Phe Leu Ser Leu Ala Gly Asn Thr
                260                 265                 270
Tyr Gln Leu Thr Arg Gly Ile Gly Lys Asp Ile Arg Ala Leu Arg Arg
            275                 280                 285
Ala Arg Ala Asn Leu Gln Ser Val Pro His Ala Ser Ala Ser Arg Pro
 290                 295                 300
Arg Val Thr Glu Pro Ile Ser Ala Glu Ser Gly Glu Gln Val Glu Arg
 305                 310                 315                 320
Val Asn Glu Pro Ser Ile Leu Glu Met Ser Arg Gly Val Lys Leu Thr
                325                 330                 335
Asp Val Ala Pro Val Ser Phe Phe Leu Val Leu Asp Val Val Tyr Leu
                340                 345                 350
Val Tyr Glu Ser Lys His Leu His Glu Gly Ala Lys Ser Glu Thr Ala
            355                 360                 365
Glu Glu Leu Lys Lys Val Ala Gln Glu Leu Glu Glu Lys Leu Asn Ile
            370                 375                 380
Leu Asn Asn Asn Tyr Lys Ile Leu Gln Ala Asp Gln Glu Leu
 385                 390                 395

<210> SEQ ID NO 8
<211> LENGTH: 396
<212> TYPE: PRT
<213> ORGANISM: Homo sapiens
<220> FEATURE:
<221> NAME/KEY: MISC_FEATURE
<222> LOCATION: (1)..(396)
<223> OTHER INFORMATION: Apo L 1 Variant

<400> SEQUENCE: 8
```

```
Met Glu Gly Ala Ala Leu Leu Arg Val Ser Val Leu Cys Ile Trp Met
1               5                   10                  15

Ser Ala Leu Phe Leu Gly Val Arg Val Arg Ala Glu Glu Ala Gly Ala
            20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Thr Asp Asn Glu Ala Trp Asn Gly
            85                  90                  95

Phe Val Ala Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
    195                 200                 205

Glu Pro Gly Met Glu Leu Gly Ile Thr Ala Ala Leu Thr Gly Ile Thr
210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
    275                 280                 285

Ala Arg Ala Asn Leu Gln Ser Val Pro His Ala Ser Ala Ser Arg Pro
290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
    355                 360                 365

Glu Glu Leu Lys Lys Val Ala Gln Glu Leu Glu Lys Leu Asn Ile
370                 375                 380

Leu Asn Asn Lys Ile Leu Gln Ala Asp Gln Glu Leu
385                 390                 395

<210> SEQ ID NO 9
<211> LENGTH: 398
```

```
<212> TYPE: PRT
<213> ORGANISM: Homo sapiens
<220> FEATURE:
<221> NAME/KEY: MISC_FEATURE
<222> LOCATION: (1)..(398)
<223> OTHER INFORMATION: Apo L 1 variant

<400> SEQUENCE: 9
```

Met Glu Gly Ala Ala Leu Leu Arg Val Ser Val Leu Cys Ile Trp Met
1               5                   10                  15

Ser Ala Leu Phe Leu Gly Val Arg Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
        130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
        290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Gly Phe Phe Leu Val Leu Asp Val Val Tyr Leu
            340                 345                 350

Val Tyr Glu Ser Lys His Leu His Gly Ala Lys Ser Glu Thr Ala
        355                 360                 365

Glu Glu Leu Lys Lys Val Ala Gln Glu Leu Glu Glu Lys Leu Asn Met

-continued

```
                    370                 375                 380
Leu Asn Asn Asn Tyr Lys Ile Leu Gln Ala Asp Gln Glu Leu
385                 390                 395
```

WILD-TYPE APOLIPOPROTEIN L-I FOR USE IN THE PREVENTION OF KIDNEY DISEASES

This application is a National Stage Application of PCT/EP2012/052731, filed 17 Feb. 2012, which claims benefit of Serial No. 11154776.6, filed 17 Feb. 2011 in the European Patent Office and which applications are incorporated herein by reference. To the extent appropriate, a claim of priority is made to each of the above disclosed applications.

FIELD OF THE INVENTION

The present invention is in the field of Molecular Biology and is related to a pharmaceutical (therapeutical or prophylactic) use of apolipoprotein L-I, especially for a treatment and/or a prevention of diseases affecting the kidney such as glomerulosclerosis.

BACKGROUND OF THE INVENTION AND STATE OF THE ART

Normal human serum (NHS) is able to kill *T. b. brucei*, but not *T. b. rhodesiense* and *T. b. gambiense*. The lytic factor was identified as being apolipoprotein L-I (apoL1) that forms pore in endosomal membranes of the parasite. This protein is associated with HDL particles that are efficiently taken up by the parasite through specific binding to a haptoglobin-hemoglobin surface receptor, due to the simultaneous presence of haptoglobin-related protein (Hpr) acting as a ligand in these particles.

The *T. brucei* subspecies *rhodesiense* and *gambiense* resist this lytic activity and can infect humans, causing sleeping sickness. *T. b. rhodesiense* resistance to lysis involves interaction of the Serum Resistance-Associated (SRA) protein with the C-terminal helix of apoL1.

SUMMARY OF THE INVENTION

The present invention discloses a therapeutic composition for patients suffering from a renal disease, possibly in relation with (caused by) a mutation in ApoL1 gene in this patient and preferably wherein this mutated ApoL1 protein is able to kill *T. b. rhodesiense* cells.

A first aspect of the present invention is related to the wild-type human Apolipoprotein L-I (SEQ ID NO:1, SEQ ID NO:4 or SEQ ID NO:7) for use in the treatment and/or the prevention of renal diseases.

Preferably, this wild-type human Apolipoprotein L-I is for use in the treatment and/or the prevention of renal diseases affecting a human patient, wherein this human patient harbours a mutated (variant) human Apolipoprotein L-I.

More preferably, this wild-type human Apolipoprotein L-I is for use in the treatment and/or the prevention of renal diseases affecting a human patient harbouring a mutated human Apolipoprotein L-I, wherein this mutated human Apolipoprotein L-I corresponds to the wild-type human Apolipoprotein sequence (SEQ ID NO:1, SEQ ID NO:4 or SEQ ID NO:7) modified by (which comprises) a deletion of 1, 2, 3, 4, 5, 6, 7, 8, 9, 10, 11, 12, 13, 14, 15, 16, 17, 18, 19 or 20 (preferably 9) of its last C-terminal amino acids and/or wherein this mutated human Apolipoprotein L-I is selected from the group consisting of SEQ ID NO:2, SEQ ID NO:3, SEQ ID NO:5, SEQ ID NO:6, SEQ ID NO:8, and SEQ ID NO:9 and more preferably being selected from the group consisting of SEQ ID NO:2, SEQ ID NO:5 and SEQ ID NO:8.

Alternatively or in addition, this wild-type human Apolipoprotein L-I is for use in the treatment and/or the prevention of renal diseases affecting a human patient harbouring a mutated human Apolipoprotein L-I, wherein this mutated human Apolipoprotein L-I is able to lyse *Trypanosoma brucei rhodesiense* cells.

Possibly, this wild-type human Apolipoprotein L-I for use in the treatment and/or the prevention of renal diseases affecting a human patient harbouring a mutated human Apolipoprotein L-I, wherein the mutated human Apolipoprotein L-I is not able to lyse *Trypanosoma brucei gambiense* cells, but preferably is able to lyse *Trypanosoma brucei rhodesiense* cells.

Advantageously, this wild-type human Apolipoprotein L-I is administered at a concentration comprised between (about) 100 μg/ml and (about) 20 mg/ml.

Possibly, this wild-type human Apolipoprotein L-I is a recombinant protein.

Alternatively (or in addition), this wild-type human Apolipoprotein L-I is present on HDL particles.

Preferably, these HDL particles comprise particles having a density comprised between 1.123 g/ml and 1.21 g/ml, more preferably these HDL particles consist (essentially) of HDL particles having a density comprised between 1.123 g/ml and 1.21 g/ml.

The present invention will be described in more details in the following detailed description of the invention as non limited illustration of the present invention.

DETAILED DESCRIPTION OF THE INVENTION

The present invention discloses a new pharmaceutical composition comprising an adequate pharmaceutical carrier, a wild-type Apolipoprotein L-I (in the form of an amino acid sequence, or a nucleotide sequence(s), a vector, a cell, a blood sample and/or particles including HDL particles) and/or fragments thereof that could be administrated to mammals, especially to humans to cure and/or prevent diseases affecting the kidney (possibly in the treatment and/or prevention of glomerulosclerosis including focal segmental glomerulosclerosis (FSGS) cause of idiopathic nephrotic syndrome, HIV associated nephropathy and hypertension associated end-stage kidney disease (ESKD) in these mammals, especially in humans.

The present invention is further related to a diagnostic method comprising the steps of:
  analysing a blood sample (obtained from a human patient) for mutation (variant) in Apolipoprotein L-I through its capacity of lysis of a *Trypanosoma brucei rhodesiense* culture;
  deducing whether this patient is carrying the mutation (variance) in Apolipoprotein L-I, possibly due to the specific lysis of *Trypanosoma brucei rhodesiense* cells.

Alternatively (or in addition) the present invention is related to this diagnostic method (further) comprising the step of performing the sequencing of the ApoL1 gene from the (blood) sample and possibly deducing whether this patient carries a mutation (variance) in ApoL1 gene.

Preferably in this diagnostic method, the two genes (chromosomal copies) of ApoL1 are sequenced and the possible deduction step discriminates between patient expressing a mutated (variant) ApoL1 at heterozygous levels (in addition to a wild-type ApoL1) and patient expressing two mutated copies of ApoL1 (possibly these two copies of ApoL1 have the same mutation and the patient is homozygous), and no wild-type ApoL1, these patients being the most affected by the renal disease.

Alternatively (but less preferably), a related diagnostic method comprises the step of:
- analysing a blood sample (obtained from a human patient) for mutation (variance) in Apolipoprotein L-I through its absence of binding to Serum Resistance-Associated (SRA) protein (of *Trypanosoma brucei rhodesiense*);
- deducing whether the patient is carrying the mutation (variance) in Apolipoprotein L-I. This method can be combined with the above-described preferred diagnostic methods.

Preferably, in these diagnostic methods, the (blood) sample is obtained from a patient suffering for a renal disease and/or who is suspected to develop a renal disease.

Preferably, in these diagnostic methods, the blood sample is obtained from a patient being at an early stage of a renal disease.

Preferably, in these diagnostic methods, the mutation (variance) in Apolipoprotein L-I corresponds to wild-type human Apolipoprotein L-I (SEQ ID NO:1, SEQ ID NO:4 or SEQ ID NO:7) modified by (which comprises) a deletion of 1, 2, 3, 4, 5, 6, 7, 8, 9, 10, 11, 12, 13, 14, 15, 16, 17, 18, 19 or 20 (preferably 9) of its last C-terminal amino acids and/or this mutated Apo L-I is selected from the group consisting of SEQ ID NO:2, SEQ ID NO:3, SEQ ID NO:5, SEQ ID NO:6, SEQ ID NO:8, and SEQ ID NO:9, being more preferably selected from the group consisting of SEQ ID NO:2, SEQ ID NO:5 and SEQ ID NO:8.

A related aspect of the present invention is a diagnostic kit comprising means to detect whether a patient carries a mutated (variant of) ApoL1, these means being selected from the group consisting of immobilized SRA, *Trypanosoma brucei rhodesiense* cells or extracts thereof, nucleotidic probes specifically recognizing the mutations (variance) in ApoL1, antibodies specifically recognizing the mutations (variance) in ApoL1 and tools for the sequencing of ApoL1 gene or messenger RNA.

Possibly, this diagnostic kit comprises:

nucleotide probes able to identify the mutated (variants) Apolipoprotein L-I or antibodies specifically recognizing mutated (variant) Apolipoprotein L-I and/or

*Trypanosoma brucei rhodesiense* culture and means to identify whether a subject is expressing the mutated (variant) Apolipoprotein L-I, wherein this mutated (variants) human Apolipoprotein L-I corresponds to the wild-type human Apolipoprotein sequence (SEQ ID NO:1, SEQ ID NO:4 or SEQ ID NO:7) modified by (which comprises) a deletion of 1, 2, 3, 4, 5, 6, 7, 8, 9, 10, 11, 12, 13, 14, 15, 16, 17, 18, 19 or 20 (preferably 9) of its last C-terminal amino acids and/or wherein this mutated (variant) human Apolipoprotein L-I is selected from the group consisting of SEQ ID NO:2, SEQ ID NO:3, SEQ ID NO:5, SEQ ID NO:6, SEQ ID NO:8, and SEQ ID NO:9 and more preferably being selected from the group consisting of SEQ ID NO:2, SEQ ID NO:5 and SEQ ID NO:8.

Another aspect of the present inventions relates to a pharmaceutical composition (including a vaccine) comprising an adequate pharmaceutical carrier (or diluent and possibly one or more adequate adjuvant(s)) and a sufficient amount of an element selected from the group consisting of the (wild-type) Apolipoprotein L-I (amino acid sequence; SEQ ID NO:1, SEQ ID NO:4, SEQ ID NO:7)), the corresponding polynucleotide or vector, or the cell expressing (an active fragment of) this (wild-type) Apolipoprotein L-I (possibly in the form of a pharmaceutically-acceptable lysate or lyophilisate); preferably, this pharmaceutical composition is used in (for) a treatment and/or a prevention of a disease affecting the kidney of a human patient.

Preferably, the pharmaceutical composition is a solution comprising the (wild-type) Apolipoprotein L-I (SEQ ID NO:1, SEQ ID NO:4, SEQ ID NO:7) at concentrations between (about) 100 ng/ml and (about) 20 mg/ml, more preferably at concentrations between (about) 10 μg/ml and (about) 10 mg/ml, still more preferably at concentrations between (about) 100 μg/ml and (about) 1 mg/ml.

The inventors used preferably the (pharmaceutical composition comprising the) wild-type ApoL1 at concentrations between (about) 10 μg/ml and (about) 20 mg/ml and still more preferably at (about) 2 mg/ml and (about) 10 mg/ml.

Advantageously, the wild-type ApoL1 is recombinant.

Preferably, the wild-type (recombinant) ApoL1 is not denaturated, such as by mixture with (about 8 M) urea.

A related aspect of the invention is a pharmaceutical composition comprising a blood sample (preferably a serum) or extract thereof comprising the (wild-type) Apolipoprotein L-I.

Preferably this blood sample or extract thereof is in the form of (HDL) particles, more preferably, being (essentially; i.e. at more than 50%, preferably more than 60%, more preferably more than 90%) in the form of HDL particles having a density comprised between 1.12 g/ml and 1.21 g/ml.

Preferably, this blood sample (serum or extract, including in the form of (HDL) particles) is for use in the treatment or the prevention of diseases affecting the kidney of a patient (more preferably a human).

Preferably, this patient has a mutated ApoL1 protein, and more preferably the patient does not express wild-type ApoL1, i.e. for instance the patient carries a mutation on both (chromosomal) copies of ApoL1 (possibly the patient is homozygous and expresses two identically mutated ApoL1 proteins).

More preferably, the mutated ApoL1 protein (present in a blood sample of the patient) is able to kill (in vitro) *Trypanosoma brucei rhodesiense* cells or *Trypanosoma* mutants having a similar phenotype.

Alternatively, or in addition, the patient expresses a mutated ApoL1 protein corresponding to wild-type human Apolipoprotein L-I (SEQ ID NO:1, SEQ ID NO:4 or SEQ ID NO:7) modified by (which comprises) a deletion of 1, 2, 3, 4, 5, 6, 7, 8, 9, 10, 11, 12, 13, 14, 15, 16, 17, 18, 19 or 20 (preferably 9) of its last C-terminal amino acids and/or this mutated Apo L-I is selected from the group consisting of SEQ ID NO:2, SEQ ID NO:3, SEQ ID NO:5, SEQ ID NO:6, SEQ ID NO:8, and SEQ ID NO:9, being more preferably selected from the group consisting of SEQ ID NO:2, SEQ ID NO:5 and SEQ ID NO:8 (and preferably the patient does not express the wild-type ApoL1).

Another aspect of the present invention is a therapeutic method to prevent and/or cure renal disease, comprising the steps of:

selecting a (human) patient having or suspected to have a renal disease;

analysing a blood sample (obtained from this patient) for the presence of mutations in ApoL1 protein (preferably carrying the mutations on the two ApoL1 genes of this patient and/or analysing the absence of wild-type ApoL1);

treating this patient having or suspected to have a renal disease and preferably having a mutation in ApoL1 protein by wild-type ApoL1 protein and/or by a nucleotide sequence encoding this wild-type ApoL1 protein.

The inventors found various naturally-occurring deletions and mutations in the C-terminal domain of apoL1 (the mutated ApoL1 of the present invention) and studied their effect on the trypanolytic potential of these mutated proteins against *T. b. brucei* and *T. b. rhodesiense*.

The inventors then screened patients that carry mutated (variants of) ApoL1 (patients that express the ApoL1 of the invention, being heterozygotes or, more preferably, patients expressing mutated ApoL1 and not wild-type ApoL1, possibly this patient is homozygous and/or express the mutated ApoL1 of the present invention).

The inventors then draw correlations between the trypanolytic potential of the mutated form (variant) of ApoL1 and the development of renal syndromes.

In addition, rodent expressing the mutated ApoL1 of the present invention were investigated for their renal pathologies and for the development of corresponding treatments.

The inventors ran in parallel cell models of kidney disease and provoked kidney disease by the addition of the mutated ApoL1 they fermented.

The inventors then added wild-type ApoL1 protein to these transgenic animals and to these cells and observed an overall tendency towards a reduction and/or delay of the renal symptoms.

Finally, the inventors administered ApoL1 to human patients suffering for a renal disease and carrying a mutation according to the invention and observed a tendency towards a reduction of the symptoms and/or to the progression of the disease.

The invention claimed is:

1. A method for the treatment of a renal disease affecting a human patient harboring a mutated human Apolipoprotein L-I comprising the step of administering to said human patient a wild-type human Apolipoprotein L-I, wherein said wild-type human Apolipoprotein L-I comprises a sequence selected from a group consisting of (SEQ ID NO:1, SEQ ID NO:4 and SEQ ID NO:7).

2. The method of claim 1, wherein said mutated human Apolipoprotein L-I corresponds to the wild-type human Apolipoprotein sequence (SEQ ID NO:1, SEQ ID NO:4 or SEQ ID NO:7) modified by a deletion of 1, 2, 3, 4, 5, 6, 7, 8, 9, 10, 11, 12, 13, 14, 15, 16, 17, 18, 19 or 20 of the last C-terminal amino acids and/or wherein said mutated human Apolipoprotein L-I is selected from the group consisting of SEQ ID NO:2, SEQ ID NO:3, SEQ ID NO:5, SEQ ID NO:6, SEQ ID NO:8, and SEQ ID NO:9.

3. The method of claim 1, wherein said mutated human Apolipoprotein L-I lyses *Trypanosoma brucei rhodesiense* cells.

4. The method of claim 3, wherein the mutated human Apolipoprotein L-I does not lyse *Trypanosoma brucei gambiense* cells.

5. The method of claim 1, wherein said human patient does not express wild-type human Apolipoprotein L-I.

6. The method of claim 1, wherein the renal disease is glomerulosclerosis.

7. The method of claim 1, wherein the wild-type human Apolipoprotein L-I is in a concentration between 100 μg/ml and 20 mg/ml.

8. The method of claim 1, wherein the wild-type human Apolipoprotein L-I is a recombinant protein.

9. The method of claim 1, wherein the wild-type human Apolipoprotein L-I is on HDL particles.

10. The method of claim 9, wherein the HDL particles consist essentially of particles having a density between 1.123 g/ml and 1.21 g/ml.

11. A method for the treatment of a renal disease affecting a human patient harboring a mutated human Apolipoprotein L-I comprising the step of administering to said human patient a nucleotide sequence encoding wild-type human Apolipoprotein L-I protein, wherein said protein sequence is selected from the group consisting of SEQ ID NO:1, SEQ ID NO:4 or SEQ ID NO:7.

12. The method of claim 11, wherein the nucleotide sequence is in the form of a vector.

13. The method of claim 12, wherein the nucleotide sequence is a plasmid.

* * * * *